US008066444B2

(12) United States Patent
Rippl et al.

(10) Patent No.: US 8,066,444 B2
(45) Date of Patent: Nov. 29, 2011

(54) DISPOSABLE WIPE WITH SUBSTANCE-FILLED BLISTERS

(75) Inventors: Carl G. Rippl, Appleton, WI (US); Chi Hao P. Duong, Austin, TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1342 days.

(21) Appl. No.: 11/607,224

(22) Filed: Nov. 30, 2006

(65) Prior Publication Data

US 2008/0127994 A1 Jun. 5, 2008

(51) Int. Cl.
*B43K 5/12* (2006.01)
(52) U.S. Cl. .............................. 401/194; 401/133; 604/3
(58) Field of Classification Search .......... 401/132–135, 401/194; 604/3; 132/320
See application file for complete search history.

(56) References Cited

U.S. PATENT DOCUMENTS

| | | | |
|---|---|---|---|
| 1,332,985 A * | 3/1920 | Jarrett | 206/222 |
| 2,209,914 A | 7/1940 | Gerber et al. | |
| 2,779,465 A | 1/1957 | Anderson | |
| 3,060,486 A | 10/1962 | Lewis | |
| 3,196,478 A | 7/1965 | Baymiller et al. | |
| 3,334,374 A | 8/1967 | Watkins, Jr | |
| 3,334,790 A | 8/1967 | Eaton | |
| 3,472,675 A | 10/1969 | Gordon et al. | |
| 3,635,567 A | 1/1972 | Richardson, Jr. | |
| 3,636,922 A | 1/1972 | Ketner | |
| 3,686,701 A | 8/1972 | Charle et al. | |
| 3,738,762 A * | 6/1973 | Moore et al. | 401/186 |
| 4,448,704 A | 5/1984 | Barby et al. | |
| 4,475,835 A | 10/1984 | Verboom et al. | |
| 4,515,703 A | 5/1985 | Haq | |
| 4,563,103 A | 1/1986 | Van Overloop et al. | |
| 4,596,481 A | 6/1986 | Tanaka | |
| 4,600,620 A | 7/1986 | Lloyd et al. | |
| 4,657,802 A | 4/1987 | Morman | |
| 4,762,124 A | 8/1988 | Kerch et al. | |
| 4,775,372 A | 10/1988 | Wilberg | |
| 4,878,775 A | 11/1989 | Norbury et al. | |
| 4,998,671 A | 3/1991 | Leifheit | |
| 5,090,832 A | 2/1992 | Rivera et al. | |

(Continued)

FOREIGN PATENT DOCUMENTS

FR 2 754 744 A1 4/1998

(Continued)

OTHER PUBLICATIONS

Lide, David R., Ph. D., Editor, *CRC Handbook of Chemistry & Physics*, 74th Edition, CRC Press, Ann Arbor, Michigan, 1993-1994, pp. 7-1, 7-3, 7-30, 8-17, 8-18, 16-24, 16-25, 16-26.

*Primary Examiner* — David Walczak
(74) *Attorney, Agent, or Firm* — R. Joseph Foster, III

(57) ABSTRACT

A device including a base layer; a wipe layer attached to the base layer to define an interior space between the wipe and base layers; a plurality of blisters positioned within the interior space, each blister having a blister volume, wherein the sum of the blister volumes is a total blister volume; and an indication disposed on the wipe layer or the base layer corresponding to a single blister or a group of blisters indicating the ratio of the blister volume of that single blister or the sum of the blister volumes of that group of blisters to the total blister volume is disclosed.

7 Claims, 4 Drawing Sheets

U.S. PATENT DOCUMENTS

| | | |
|---|---|---|
| 5,639,532 A | 6/1997 | Wells |
| 5,641,507 A | 6/1997 | Devillez |
| 5,695,868 A | 12/1997 | McCormack |
| 5,791,801 A * | 8/1998 | Miller .......................... 401/132 |
| 5,833,061 A | 11/1998 | Storandt |
| 5,843,056 A | 12/1998 | Good et al. |
| 5,902,433 A | 5/1999 | Becher et al. |
| 5,957,605 A | 9/1999 | Cohen et al. |
| 6,145,155 A | 11/2000 | James et al. |
| 6,170,426 B1 | 1/2001 | Thorsbakken |
| 6,305,044 B1 | 10/2001 | James et al. |
| 6,315,482 B1 | 11/2001 | Girardot et al. |
| 6,322,271 B1 | 11/2001 | Girardot et al. |
| 6,406,206 B1 | 6/2002 | Girardot et al. |
| 6,491,928 B1 | 12/2002 | Smith, III |
| 6,508,604 B1 | 1/2003 | Bechmann et al. |
| 6,547,468 B2 | 4/2003 | Gruenbacher et al. |
| 6,588,961 B2 | 7/2003 | Lafosse-Marin et al. |
| 6,607,739 B1 | 8/2003 | Wallo |
| 6,726,386 B1 | 4/2004 | Gruenbacher et al. |
| 6,811,338 B1 | 11/2004 | Gruenbacher et al. |
| 6,863,960 B2 | 3/2005 | Curro et al. |
| 6,945,253 B2 | 9/2005 | Michel et al. |
| 6,993,805 B2 | 2/2006 | Prodoehl et al. |
| 7,020,927 B2 | 4/2006 | Calvillo |
| 7,021,848 B1 | 4/2006 | Gruenbacher et al. |
| 7,033,100 B2 * | 4/2006 | Barton et al. ..................... 401/7 |
| 2002/0189040 A1 | 12/2002 | Svendsen |
| 2005/0065056 A1 | 3/2005 | Cook et al. |
| 2005/0255016 A1 | 11/2005 | Svendsen et al. |
| 2006/0064830 A1 | 3/2006 | Sigl et al. |
| 2006/0147250 A1 | 7/2006 | Tereschouk |
| 2006/0171997 A1 | 8/2006 | Gruenbacher et al. |

FOREIGN PATENT DOCUMENTS

| | | |
|---|---|---|
| WO | WO 2005/094711 A2 | 10/2005 |
| WO | WO 2007/040843 A2 | 4/2007 |

\* cited by examiner

DISPOSABLE WIPE WITH SUBSTANCE-FILLED BLISTERS

BACKGROUND

This disclosure pertains to cleaning, absorbent, and application devices, and containers for liquids.

As consumers become more sophisticated, they look for new cleaning products to make their lives easier. While certain combinations of substances may provide a benefit, they may not be conveniently available to consumers in a usable form because they are reactive with each other in storage. Therefore there is a need for a product form that allows novel cleaning substances to be safely and reliably provided to the consumer.

Cleaning devices and other similar devices that include a fluid container commonly include one or more bladders or liquid-containing pouches. Such pouches are designed to burst along a frangible seam or portion when pressure is applied to the device and therefore the pouch. Such devices are not selective and burst under sufficient pressure; in the case of multiple pouches within a device the user has no way of knowing how many or what percentage of pouches within the device have burst. In the case of multiple pouches containing multiple substances, the user has no way of knowing how many or which types of pouches within the device have burst.

SUMMARY

Cleaning devices and other similar devices including bladders that contain fluids suffer from the problem of premature bursting of such liquid containing pouches. Such devices also suffer from the problem of a user not knowing how many, what percentage of, or which pouches within the device have burst.

This disclosure solves these bursting problems by providing a device including soft flexible blisters of fluids. The device is also provided with indicators corresponding to the flexible blisters such that a user can know how many, what percentage of, or which blisters within the device have burst.

More specifically, the present disclosure provides a device including a base layer; a wipe layer attached to the base layer to define an interior space between the wipe and base layers; a plurality of blisters positioned within the interior space, each blister having a blister volume, wherein the sum of the blister volumes is a total blister volume; and an indication disposed on the wipe layer or the base layer corresponding to a single blister or a group of blisters indicating the ratio of the blister volume of that single blister or the sum of the blister volumes of that group of blisters to the total blister volume.

The present disclosure also provides a device including a base layer; a wipe layer attached to the base layer to define an interior space between the wipe and base layers; a first substance blister positioned within the interior space, the first substance blister including a first substance; a second substance blister positioned within the interior space, the second substance blister including a second substance; a first indication corresponding to the first substance blister; and a second indication corresponding to the second substance blister.

The present disclosure also provides a method for using a device, the method including producing a device including a base layer; a wipe layer attached to the base layer to define an interior space between the wipe and base layers; a first substance blister positioned within the interior space, the first substance blister including a first substance; a second substance blister positioned within the interior space, the second substance blister including a second substance; a first indication disposed on the wipe layer or the base layer corresponding to the first substance blister; and a second indication disposed on the wipe layer or the base layer corresponding to the second substance blister. The method also includes providing instructions to a consumer with respect to which blisters to burst based on the consumer's needs.

The purposes and features of the present disclosure will be set forth in the description that follows. Additional features of the disclosure may be realized and attained by the product and processes particularly pointed out in the written description and claims hereof, as well as from the appended drawings.

It is to be understood that both the foregoing general description and the following detailed description are exemplary and are intended to provide further explanation of the disclosure claimed. The accompanying drawings, which are incorporated in and constitute part of this specification, are included to illustrate and provide a further understanding of the disclosure.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

Figure 1:
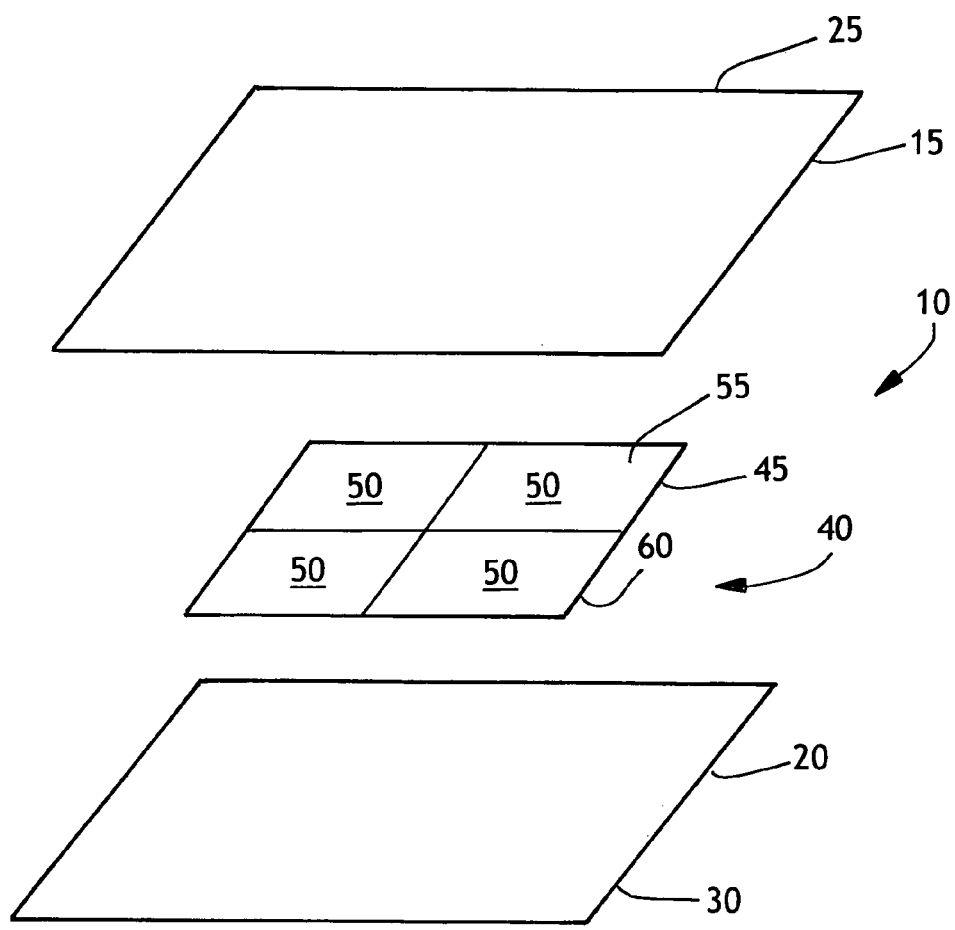
FIG. 1 is an exploded schematic perspective view of an article of the present disclosure.

Repeat use of reference characters in the present specification and drawings is intended to represent the same or analogous features or elements of the present disclosure. The drawings are representational and are not necessarily drawn to scale. Certain proportions thereof may be exaggerated, while others may be minimized.

DETAILED DESCRIPTION OF THE DISCLOSURE

The aspects of the disclosure as described herein will be described for exemplary purposes as a cleaning device. The aspects of the disclosure, however, apply equally to other forms of products, including absorbent devices, application devices, personal care devices, cosmetic devices, and other devices including wipes, mops, mitts, and cleaning towels, among other devices, and to all suitable uses including cleaning, applying, and removing.

The term "surface" and its plural generally refer herein to the outer or the topmost boundary of an object. Surface may refer to that of skin, hair, clothing, upholstery, countertops, floors, walls, windows, tables, appliances, bathroom fixtures, automobiles, or any other object that may require or accommodate cleaning, removing something from, or applying something to its surface.

As used herein, the term "device" means any flexible structure adapted to be used in conjunction with a hand or a tool to clean a surface, or to apply or remove a substance from a surface. Advantageously, the structure may be generally flat and have distinct opposing sides. A chemical or other substance may be included with the device. The device may take the form of a mitt, a wipe, a tool cover, or any other suitable form. The portions of the structure including the different substances may be provided with visual indicia, such as color coding, to provide the user with guidance for proper hand placement, or to determine in what order the sides are to be used.

As used herein, the term "mitt-like" means a device adapted to receive and fully or partially enclose a person's hand or a tool when the structure is being used. It may or may not have a separate opening or other accommodation for a thumb and/or one or more fingers for stability or control during use. However, the structure may also be generally cylindrical, somewhat like a sock, such that the opposing sides result from the position of the user's hand within. In such a case, the portion of the structure contacting the palm of the hand becomes one side of the mitt-like device and the portion of the structure contacting the back of the hand becomes the opposing side. The mitt-like device can be sized to fit over one or multiple fingers.

As used herein, the term "wipe" means a device adapted to be held by a user or a tool but that is not adapted to receive and fully or partially enclose a person's hand when the structure is being used.

As used herein, the terms "target surface" and "surface" refer to the surface upon which the device is acting and treating. The term "surface" and its plural generally refer herein to the outer or the topmost boundary of an object. Surface may refer to that of skin, hair, fur, clothing, upholstery, countertops, floors, walls, windows, tables, appliances, bathroom fixtures, automobiles, or any other object that may require or accommodate bathing, cleaning, removing something from, or applying something to its surface. The term is used to distinguish from and avoid confusion with references to the various surfaces of the device.

Described herein is a disposable device 10 for the removal of dirt, etc. from or the application of a substance to a surface. Such a device 10 allows a user to clean or treat a surface.

FIG. 1 illustrates an example of a device 10 as an aspect of the present disclosure. The device 10 includes a wipe layer 15 and a base layer 20. For purposes of illustration, and not for purposes of limitation, the device 10 is described as a wipe.

The device 10 includes a wipe layer 15. The wipe layer 15 may be of any suitable shape, but is preferably generally planar and is further preferably generally rectangular or oblong. The wipe layer 15 has a perimetric edge 25 extending around the wipe layer 15. In one aspect of the present disclosure, the wipe layer 15 is generally the size of a human hand held flat on a surface. In another aspect of the present disclosure, the wipe layer 15 is generally the size of the four fingers of a human hand. In still another aspect of the present disclosure, the wipe layer 15 is generally the size of a human finger. The device 10 may be manufactured in any shape or of any dimensions, including as a wipe sized to fit best in a child's hand, an adult hand, or on any cleaning implement. In general, the wipe layer 15 may be of any suitable size, with the size preferably selected to be suitable for the intended use of the device 10. In other aspects of the present disclosure, the device 10 can be manufactured into other shapes such as a mitt or square or round wipes, etc.

The wipe layer 15 is an active layer, which performs the cleaning function. The wipe layer 15 is stretchable, and may be either elastically or plastically stretchable. In alternate aspects of the present disclosure, any suitable coform, nonwoven, or woven material may be used. In one aspect of the present disclosure, the wipe layer 15 is an absorbent material. The wipe layer 15 may be a stretch-bonded laminate (SBL) with pre-stretched elastic filament and meltblown material with one ply of spunbond material on each outer surface and a basis weight of approximately 70 gsm, but any suitable absorbent material may be used. SBL and other composite nonwoven elastic webs are further described in U.S. Pat. No. 4,657,802 to Morman. In one aspect of the present disclosure, the wipe layer 15 includes a dry embossed 110 grams per square meter (gsm) coform laminate available from Kimberly-Clark Corporation.

In other aspects of the present disclosure, materials for the wipe layer 15 may include cotton, rayon, wood pulp, and polymeric substances such as nonwoven fabrics, foam sponges, and thermoplastics. The material may be formed of a nonwoven fabric that is made of interbonded thermoplastic fibers. The fibers may be formed from a variety of thermoplastic materials including polyolefins (e.g., polyethylene or polypropylene), polystyrene, and polyamides (e.g., nylon). In addition, thermoplastic polymers that are elastomeric may also be used as fibers, including polyurethanes and block copolymers. Blends of any of these materials may be used to form the fibers. The fibers may include additives (e.g., wax, pigments, stabilizers, and fillers) that are inserted as the fibers are fabricated to achieve one or more desired properties within the fibers. Some example additives include compatible surfactants that are added to the polymers to make the surface of the fibers more wettable, thereby improving the ability of the fiber structure to attract unwanted debris away from the skin. The amount of surfactant added to the fibers can be adjusted to control the surface wetting of the fabric formed from the fibers. Examples of suitable surfactants include sodium dioctyl sulfosuccinate and alkyl phenoxy ethanol.

Material used in making the wipe layer 15 may be capable of capturing and/or storing substances within the material. Such material may store and/or capture debris, cleansers, lubricants, spermicidal agents, and medications, among other materials, before or while using the device 10. Examples of such materials include spunbond, spunlace, bonded carded web, and apertured film materials. In one aspect of the present disclosure, the material is an apertured film that is formed of a polyolefin that may be combined with a nonwoven fabric. In other aspects of the present disclosure, the material of the wipe layer 15 may be a laminate of like, similar, or different tissue, nonwoven, woven, or film materials, or of any other materials described herein. With some materials such as spunlace, pulling on the ends of the device 10 may cause the device 10 to reduce in width at the middle of the device 10. Should this happen, a user may restore the shape of the device 10 by lightly pulling on the sides of the device 10.

When a nonwoven fabric is used, the basis weight of the nonwoven fabric may vary depending on the properties that are desired within the device 10. As an example, the basis weight for the nonwoven fabric may be as low as 10 gsm and as high as 300 μm. Such nonwoven materials may include a textured surface. Examples of such nonwoven textured materials include rush transfer materials, flocked materials, wireform nonwovens, and thermal point unbonded materials, among others.

In one aspect of the present disclosure, the wipe layer 15 may be used dry to absorb liquids from a surface. In another aspect of the present disclosure, the wipe layer 15 may be dampened by a user with water or another substance to aid cleaning with the device 10.

The device 10 also includes a base layer 20. The base layer 20 is preferably of the same general size and shape of the wipe layer 15, although the size and/or shape of the base layer 20 may be selected to be different from the size and/or shape of the wipe layer 15 based on the intended use of the device 10. The base layer 20 has a perimetric edge 30 extending around the perimeter of the base layer 20.

The base layer 20 may be a backing layer. The base layer 20 may be stretchable, and may be either elastically or plastically stretchable. The base layer 20 may be manufactured from any suitable nonwoven, woven, or paper tissue material. In one aspect of the present disclosure, the base layer 20 is an absorbent material. The base layer 20 may be SBL with pre-stretched filament and meltblown material with one ply of spunbond material on each outer surface and a basis weight of approximately 70 gsm, but any suitable absorbent material may be used. In one aspect of the present disclosure, the base layer 20 includes a dry embossed 100 gsm coform laminate available from Kimberly-Clark Corporation.

In an alternative aspect of the present disclosure, the base layer 20 is also an active layer and manufactured under any of the aspects of the present disclosure described above for the wipe layer 15. In the case of the base layer 20 as an active layer, the base layer 20 may be manufactured from a material similar to or different from that used for the wipe layer 15.

In an alternative aspect of the present disclosure, one or both of the wipe and base layers 15, 20 may be breathable to allow air to circulate through the device 10.

The wipe layer 15 is coupled to the base layer 20. One of the wipe and base layers 15, 20 is positioned to overlie the other of the wipe and base layers 15, 20, such that the perimetric edges 25, 30 of the wipe and base layers 15, 20 generally align. A portion of the perimetric edge 25 of the wipe layer 15 is attached to the perimetric edge 30 of the base layer 20 to form a seam 35 and an interior space 40. The seam 35 may be formed at the perimetric edges 25, 30, or the seam 35 may be adjacent or inward from the perimetric edges 25, 30. The wipe and base layers 15, 20 may be attached by adhesive, ultrasonic bonding, heating, sewing, or by any other suitable method. In one aspect of the present disclosure, the wipe and base layers 15, 20 are attached using a block copolymer adhesive such as 34-5610 construction adhesive available from National Starch & Chemical Company, Bridgewater, N.J. The construction adhesive used to attach the wipe and base layers 15, 20 may also be stretchable. The wipe and base layers 15, 20 may also be attached at locations in addition to or other than the perimetric edges 25, 30.

Coupling the wipe layer 15 to the base layer 20 forms the device 10 with an interior space 40.

The base layer 20 may include a liquid impermeable barrier layer (not shown) facing the interior space 40. In one aspect of the present disclosure, the material of the barrier layer is a polyolefin-type material that can be heat sealed or ultrasonically sealed. In another aspect of the present disclosure, the material of the barrier layer is a material such as BSTL, a breathable, stretchable, thermal laminate. BSTL and similar materials are described in U.S. Pat. No. 5,695,868 to McCormack et al. and U.S. Pat. No. 5,843,056 to Good et al. In yet another aspect of the present disclosure, the material of the barrier layer may be SBL as described above, or may be any other suitable material, particularly those described above with reference to the wipe layer 15. In one aspect of the present disclosure, because the base layer 20 is the layer most likely to contact a user's hand, the barrier layer acts to keep the base layer 20 and thus the user's hand dry. In another aspect of the present disclosure, the user's hand or one or more fingers may be inserted between the barrier layer and the base layer 20, where the barrier layer again acts to keep the user's hand/finger(s) dry. The barrier layer may also be positioned adjacent a portion of the wipe layer 15 to occlude a portion of the wipe layer 15 from fluid contact, allowing that portion of the wipe layer 15 to remain dry. Separate barrier layers may also be positioned adjacent the base layer 20 and adjacent the wipe layer 15. In another aspect of the present disclosure, the base layer 20 and the barrier layer may be the same layer.

In another aspect of the disclosure that is not shown, a distribution layer may be interposed between the blister and the wipe layer 15 to ensure fluid is distributed across the wipe layer 15. The distribution layer may be, for example, a surge material that wicks fluid to a substantial portion of the wipe layer 15.

In yet another aspect of the present disclosure, distribution of fluid into the wipe or base layers 15, 20 may be controlled by using materials with different wicking and other properties that will absorb and distribute the fluid in different patterns, rates, and manners.

By virtues of the design and materials chosen for the device 10, the device 10 is preferably designed to be disposable. In this case, disposable means that the device 10 is disposed of, rather than cleaned, after use.

In an alternative aspect of the present disclosure, the wipe layer 15 and the base layer 20 are two portions of the same piece of material. One of the wipe layer 15 and the base layer 20 is folded over the other of the wipe layer 15 and the base layer 20, and a portion of the perimetric edges 25, 30 are coupled by any means described herein to form the device 10.

In an alternative aspect of the present disclosure, an additional mitting layer (not shown) of material may be added and attached to a portion of the perimetric edges 25, 30 while leaving at least one end open to form a mitt to be worn by the user. The mitt may be sized for a human hand, or may be sized for one or more human fingers, including taking the form of a finger glove. The mitting layer can be the same size or shape as the device 10, or it may be a different size or shape, such as smaller or larger. In one aspect of the present disclosure, the mitting layer may be a strap.

The device 10 further includes a blister layer 45 including a plurality of fluid-containing blisters 50. The blister layer 45 is disposed between the wipe layer 15 and the base layer 20. In one aspect of the present disclosure, each blister 50 is formed in part by an upper blister film 55 and a lower blister film 60. The top and bottom layers 55, 65 are attached such that they form and enclose a cavity. The top and bottom layers 55, 65 may be attached by thermal bonding, although any suitable attachment method may be used. The cavity may be sealed such that it contains a fluid. The blister 50 may be rectangular, square, circular, oblong, or any other suitable size or shape.

The blister films 55, 60 may be any film that includes but is not limited to water insoluble film, oil-insoluble film, or combinations thereof, which are capable of being sealed while containing an active material enclosed therein. Although the blister films 55, 60 may possess small perforations, it is preferred that the blister film does not possess perforations having a width greater than about 0.2 mm.

The blisters 50 are made from a flexible, heat sealable material such as 2 mil polyethylene film available from Bemis Company, Inc. In other aspects of the present disclosure, the blisters 50 may be made from polyethylene, polypropylene, or other suitable thermoplastics, or from a high liquid barrier material such as a metal foil or a metalized film. The material from which the blisters 50 are made should have no negative impact on or reaction with the fluid to be contained in the blisters 50. The materials used in the construction of the blisters 50 and the fill level of the fluid within the blisters 50 create a structure that is durable and flexible, and one that is not easily burst open during normal handling.

Although a variety of blister films 55, 60 may be used to produce the blisters, it is desirable to use a film that possesses a sufficient strength to contain the active material therein during storage, but flexible enough for a consumer to puncture or "pop" through the film to enable usage of the fluid contained therein.

Each blister 50 may include an upper blister film 55 that is the same or different from the lower blister film 60 with respect to thickness, composition, etc. The thickness of the blister film may range from about 0.5 mil to about 3 mil, and preferably about 1 mil to about 2 mil. For uses of the device 10 by persons such as children, the elderly, and those of limited strength, the use of thinner blister films, i.e. less than about 2.0 mil, may be used.

Each blister may be prepared individually by securing the periphery of the blister together via suitable means, e.g., heat sealing, after the blister is loaded with the desired amount of fluid. Alternatively, one sheet of blister film may be folded upon itself or two independent blister films may be disposed on top of another, then each blister may be formed by heat sealing the blister film combination in accordance with the desired blister shape. The plurality of blisters 50 may be randomly distributed, arranged in columns, or in an array of any desired dimensions. The plurality of blisters 50 may also be disposed in only one portion of the device 10, such as in one half of the device 10, leaving the other half of the device 10 without blisters 50.

FIG. 1 illustrates an aspect of a device 10 according to the disclosure configured as a wipe. With this aspect, the blister 50 may contain, for example, a fluid composition particularly suited for cleaning any manner of surface. To enhance the cleaning effect of the device 10, the wipe layer 15 may include a textured outer face that may be formed from any suitable textured material.

For any of the blister configurations described herein, the blisters 50 are positioned within the interior space 40 of the device 10. The blisters 50 may be sealed prior to being filled or partially filled with one or more fluids. The blisters 50 may be any size that fits within the interior space 40, with the size selected based on the fluid to be housed and the intended use of the device 10.

The blisters 50 can be sized to provide a level of over saturation that permits the fluid to soak through the wipe layer 15, permitting it to be absorbed by the intended surface. An example of this would be a stain removal cloth for carpet cleaning where it is desired to soak the stain.

The device 10 may be formed by any means for attaching the wipe layer 15 to the base layer 20, either directly or indirectly, with the blister layer 45 therebetween.

More specifically, the device 10 may be made by removably attaching, or preferably substantially permanently attaching, the wipe and base layers 15, 20 by any suitable attaching means. As used herein, "substantially permanently" means a period of time at least as long as the device is suitable for its intended use. Alternatively, the wipe layer 15 may be removably or substantially permanently attached to the blister layer 45, which is then removably or substantially permanently attached to the base layer 20.

Examples of suitable attaching methods include heat sealing with a sealer capable of reaching a temperature greater than the melting temperature of the film; ultrasonic sealing; pressure sealing; sewing; applying hook and loop material; hot or cold adhesive; elastic; heat shrinkable film, or other suitable fastening means; and combinations thereof.

In another aspect of the present disclosure (not shown), the wipe layer 15 may be partially attached to the base layer 20 to form a pocket, the blister layer 45 is inserted into the pocket, and then the wipe and base layers 15, 20 are attached along the open end of the pocket. Alternatively, the blister layer 45 may be disposed between such wipe and base layers 15, 20 prior to performing the attachment. For aspects in which it is desirable to insert new blister layers 45 when the existing blister layers 45 have been expended, it is preferable to use a removably attachable attaching method along at least one side of the device 10.

In other aspects of the present disclosure, the blister layer 45 may be replaced by a plurality of blisters 50 disposed between the wipe and base layers 15, 20, wherein the blisters are burstable capsules or any other suitable burstable, fluid-containing structure. The blisters 50 in these aspects may be secured in position to either or both of the wipe and base layers 15, 20 using adhesives, bonding, or by any other suitable means.

Each blister 50 within the device 10 has a blister volume. In some aspects of the present disclosure the blister volume of each blister 50 is essentially equivalent, while in other aspects the blister volumes of some blisters 50 may be different from the blister volumes of other blisters 50. The volume of any given group of blisters is the sum of the blister volumes of each of the blisters 50 in that group. The sum of all the blister volumes in the device 10 is the total blister volume. The ratio of the volume of one blister 50 or of a group of blisters 50 to the total blister volume may be calculated by dividing the volume of the one or more blisters by the total blister volume. This ratio gives the user of the device 10 an estimate of the total volume that the user may employ by bursting less than all of the blisters 50 in the device 10. These aspects are particularly useful when all of the blisters 50 include the same substance or fluid.

Figure 2:
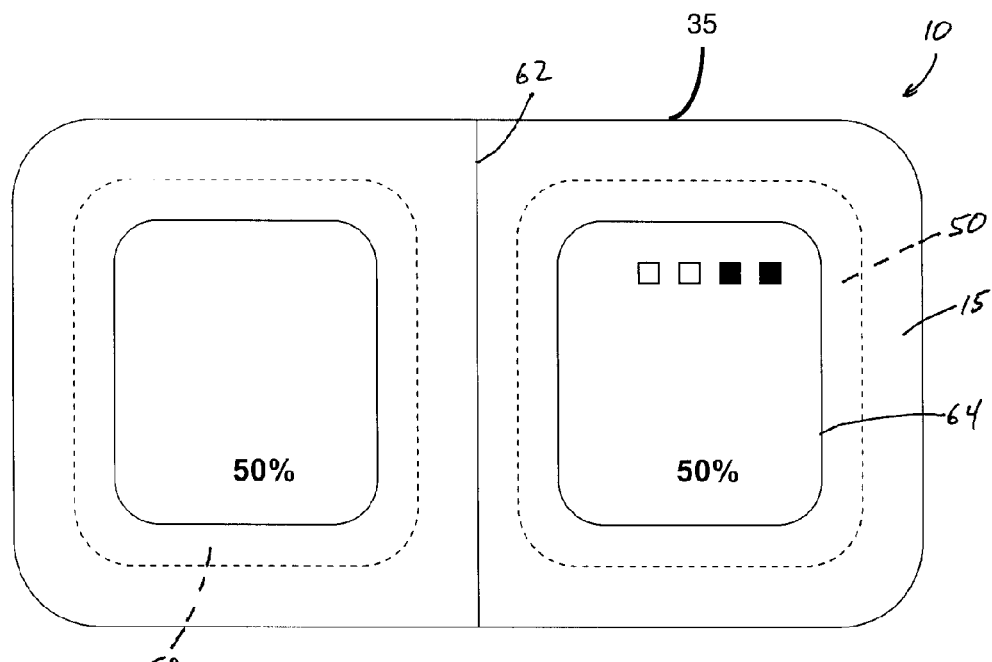
FIG. 2 is a schematic plan view of various aspects of the device of FIG. 1.

This ratio may be indicated to the user of the device 10 in any way that makes the ratio understandable. As examples, the ratio may be indicated as a fraction such as ½, as a percentage such as 50%, or graphically such as half of a circle filled in or two boxes out of four filled in, as illustrated in FIG. 2. Such an indication may also be conveyed to the user by any suitable means.

First, as illustrated in FIG. 2, the indication may include alphanumeric characters or graphics printed or otherwise placed on the wipe or base layer 15, 20 or both. A blister 50 or group of blisters 50 may be labeled with one of the indications described herein indicating to the user, for example, that bursting the blister(s) 50 labeled with 50% would release half of the total blister volume. That blister 50 or group of blisters 50 may be further indicated or differentiated by coloring on the wipe or base layer 15, 20 or on the blister layer 45, or by some combination thereof. That blister 50 or group of blisters 50 may also be further indicated or differentiated by separating that blister 50 or that group of blisters 50 from the other by lines 62, boxes 64, or any other geometric or non-geometric differentiation mechanism. It should be noted that any ratio may be used, or multiple ratios may be used, and that 50 percent was used as an example herein.

Figure 3:
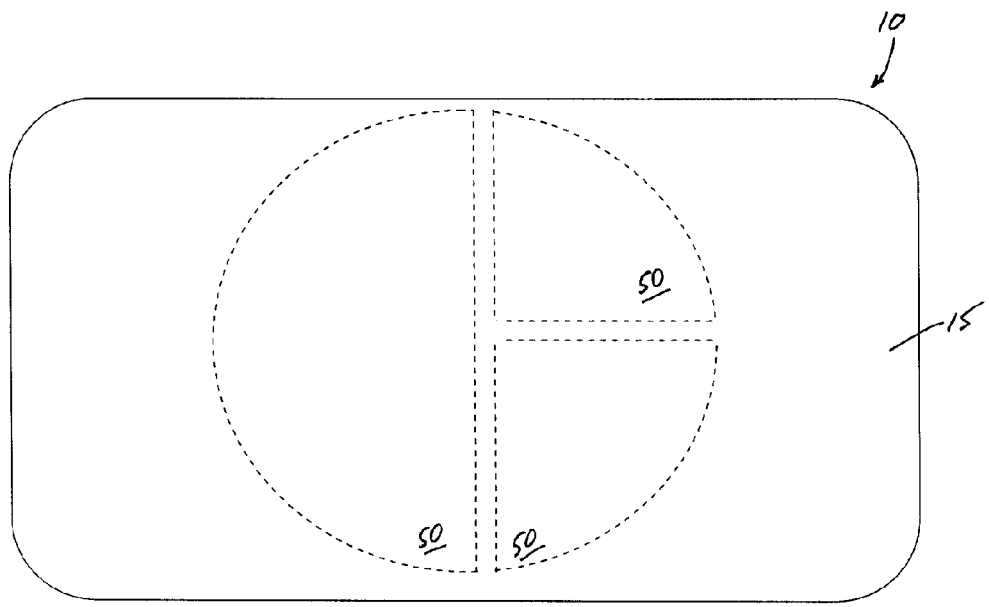
FIG. 3 is a schematic plan view of various aspects of the device of FIG. 1.

Second, the indication may include the shape of the blisters 50 with or without the addition of printing or other differentiating mechanism. For example, as illustrated in FIG. 3, two blisters 50 each shaped as quadrants of a circle and another blister 50 shaped as half of a circle, all together forming a circle, would indicate to the user that bursting either the two quadrants or the half circle, for example, would release half of the total blister volume. In a similar example, manufacturing the device 10 with one blister 50 in the shape of a circle and another blister 50 in the shape of a square could also indicate to the user that bursting either the circle or the square would release half of the total blister volume and bursting both the circle and the square would release all of the total blister volume.

Figure 4:
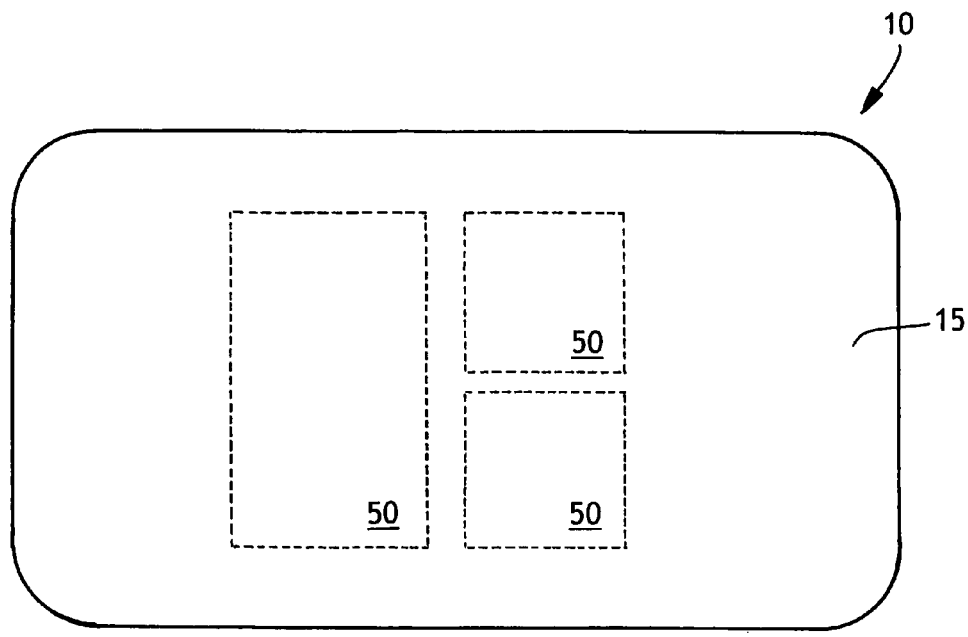
FIG. 4 is a schematic plan view of various aspects of the device of FIG. 1.

Third, the indication may include the size of the blisters 50 with or without the addition of printing or other differentiating mechanism. For example, as illustrated in FIG. 4, one blister 50 may be sized as half of a square, and two additional adjoining blisters 50 may be each sized as a remaining quadrant of that square. This arrangement would indicate to the user that bursting either the two smaller blisters 50, or the one larger blister 50, for example, would release half of the total blister volume. It should be noted that, in certain of these aspects, the shape and/or size of at least some of the blisters 50 should be apparent to a user without disassembling the device 10. The shape and/or size of a blister 50 may be made apparent by bonding techniques such as bonding the blister layer 45 to one or both of the wipe and base layers 15, 20 adjacent the blister 50, or by bonding the wipe layer 15 to the base layer 20 adjacent the blister 50. The shape and/or size of a blister 50 also may be made apparent by providing an indication on the wipe or base layers 15, 20, or both. For example, a circular blister 50 may be indicated on the wipe layer 15 by a printed circle or by a colored spot.

Figure 5:
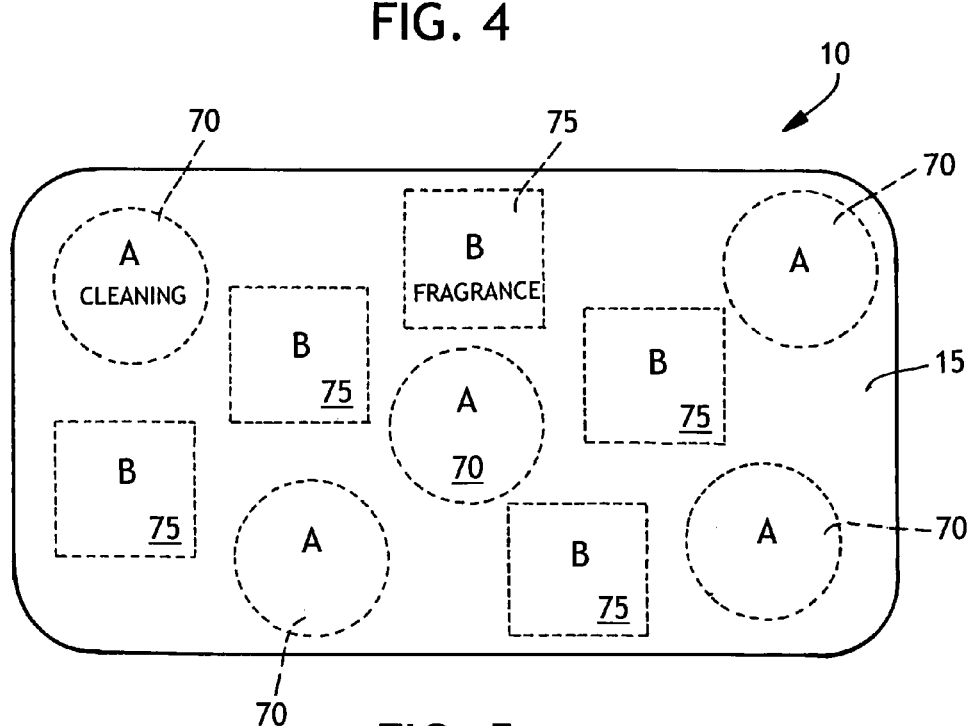
FIG. 5 is a schematic plan view of various aspects of the device of FIG. 1.

Similar aspects are available where the blisters 50 include more than one substance such as that illustrated in FIG. 5, for example the situation in which a first substance blister 70 or a group of first substance blisters 70 includes a first substance, and a second substance blister 75 or a group of second substance blisters 75 includes a second substance. The first substance blister(s) 70 including the first substance can be differentiated to the user of the device 10 from the second substance blister(s) 75 including the second substance by an indication that may include alphanumeric characters, graphics, and the shape and/or size of the blisters.

For the situation in which the indication includes alphanumeric characters or graphics, the indication may be printed or otherwise placed on the wipe or base layer 15, 20, or both. The first substance blister(s) 70 can be labeled with a letter or number, a character or other graphic, by color, by the name or function of the first substance, or by any other identifier that will differentiate the first substance to the user of the device 10. The second substance blister(s) 75 may similarly be identified in any way that will differentiate the second substance to the user of the device 10. For example, the first substance blister(s) 70, where the first substance is a cleaning solution, could be labeled "Cleaning." The second substance blister(s) 75, where the second substance is a fragrance, could be labeled "Fragrance." The user can then decide whether to simply burst the first substance blister(s) 70 including the cleaning solution, or to burst both the cleaning and fragrance blisters 70, 75. The first and second substance blisters 70, 75 may be further indicated or differentiated by coloring on the wipe or base layer 15, 20 or on the blister layer 45, or by some combination thereof. Those blisters 70, 75 may also be further indicated or differentiated by separating the first substance blister(s) 70 from the second substance blister(s) 75 by lines, boxes, or any other geometric or non-geometric differentiation mechanism similar to those illustrated in FIG. 2.

Second, as also illustrated in FIG. 5, the indication may include the shape of the blisters 50 with or without the addition of printing or other differentiating mechanism. For example, manufacturing the device 10 with a first substance blister 70 in the shape of a circle and a second substance blister 75 in the shape of a square could also indicate to the user that bursting either the circle or the square would release one substance, and bursting both the circle and the square would release both substances.

Figure 6:
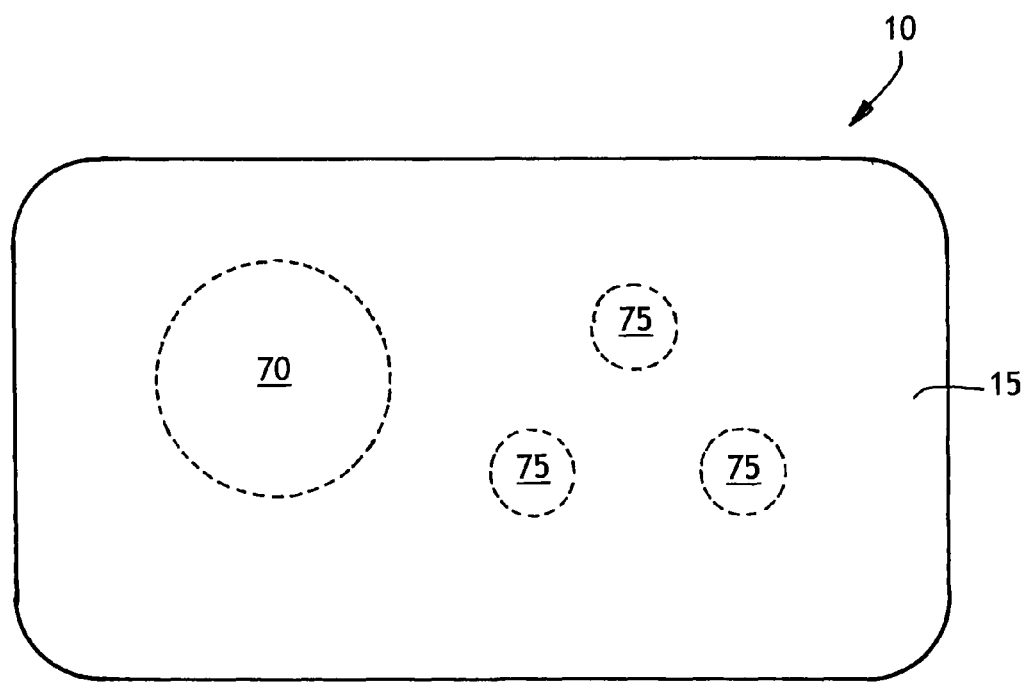
FIG. 6 is a schematic plan view of various aspects of the device of FIG. 1.

Third, the indication may include the size of the blisters 50 with or without the addition of printing or other differentiating mechanism. For example, as illustrated in FIG. 6, a first substance blister 70 may be a large circle, and a second substance blister 75 may be a small circle. This arrangement would indicate to the user that bursting either the large circle or the small circle would release one substance, and bursting both the large and small circles would release both substances.

As described above, it should be noted that, in certain of these aspects, the shape and/or size of at least some of the blisters 50 should be apparent to a user without disassembling the device 10. The shape and/or size of a blister 50 may be made apparent by bonding techniques such as bonding the blister layer 45 to one or both of the wipe and base layers 15, 20 adjacent the blister 50, or by bonding the wipe layer 15 to the base layer 20 adjacent the blister 50. The shape and/or size of a blister 50 also may be made apparent by providing an indication on the wipe or base layers 15, 20, or both. For example, a circular blister 50 may be indicated on the wipe layer 15 by a printed circle or by a colored spot. It should also be noted that the same principles of differentiation can be applied to third and subsequent blister(s) 50 including third and subsequent substances. In general, blisters 50 including similar or identical substances should be similar in indication, and blisters 50 including different substances should be differentiated in indication.

The fluid contained within each blister may be any fluid suitable for the intended use of the device 10. Substances may also be impregnated or saturated into the wipe and/or base layers 15, 20 of the device 10.

The blisters 50 may all include the same substance to be used for cleaning, painting, polishing, hydration, or any other function that may be supplied by a fluid from a device 10. Example fluids include cleansing fluids for human/animal use and cleaning fluids for cleaning surfaces. The fluid may be any paste, gel, powder, oil, liquid, or any other appropriate medium. Example cleansing fluids can include as components surfactants such as water-soluble polymers, polysorbates, glycerins, glycol-based surfactants, and/or silicone-based surfactants. The fluid may include other materials, such as water, salts, vinegars, humectants, scouring powders, thickening agents, and fragrances. A cleansing fluid may also include a moisturizer that helps to maintain a normal skin hydration level. A cleansing fluid may also include preservatives and other ingredients that do not disrupt the skin (e.g., sorbic acid, citric acid, methyl paraben, and natural preservatives such as grapefruit extract). The fluid may include other materials that may be applied to an area of the body. Example materials include lubricants, deodorants, and other inactive or active ingredients (e.g., spermicidal agent or medication). In one aspect of the present disclosure, the fluid is a cleansing fluid that is primarily a water-based solution (greater than or equal to 90 percent water content) with a surfactant, preservatives, pH neutralizers, and a thickening agent. The fluid may be a lotion or an emulsion. Non-limiting examples include sunless tanning lotion, leather conditioning lotion, and depilatory lotion.

The fluid may be a cleaning solution such as FOUR PAWS Super Strength Stain and Odor Remover, which includes water, natural enzymes, and mild detergent (from Four Paws Products, Ltd., Hauppauge, N.Y.), or NATURE'S MIRACLE Stain & Odor Remover, which includes water, natural enzymes, isopropyl alcohol, and natural citrus scent (from Pets 'N People, Inc., Rolling Hills Estates, Calif.), or RESOLVE Carpet Spot & Stain Carpet Cleaner (from Reckitt Benckiser, Wayne, N.J.). The fluid may be a pet shampoo. The fluid may be a stain cleaner and stain guard such as SCOTCH-GARD Oxy Carpet Cleaner with Stain Protector that includes water, 2-butoxyethanol, hydrogen peroxide, and surfactants (from 3M Corporation, St. Paul, Minn.). In the case of using the cleaning device 10 to clean a fabric surface, the fluid may include a pet repellant such as SIMPLE SOLUTION Indoor/Outdoor Repellent for Dogs and Cats, which has as an active ingredient methyl nonyl ketone (from The Bramton Company, Dallas, Tex.).

The fluid may be an antimicrobial. Examples of suitable antimicrobials include quaternary ammonium compounds such as 3-trimethoxysilylpropyldimethyloctadecyl ammonium chloride (AEGIS); poly cationic chemicals such as biguanides (poly (hexamethylene) biguanide hydrochloride (PHMB) Arch Chemical), 2, 4, 4'-Trichloro-2'-hydroxyldipenylether (Tinosan, Ciba); diphenyl ether (bis-phenyl) derivatives known as either 2, 4, 4'-trichloro-2' hydroxy dipenyl ether or 5-chloro-2-(2, 4-dichlorophenoxy) phenol; triclosan; silver; and copper. The fluid may be an allergen sequestrant that may be a charged or mixed charged particle or nanoparticle. Most allergy proteins are glycoproteins (proteins that contain covalently-bound oligosaccharides), so a negative charge may be better then predominance of positive charges on the particles, although mixed charges may be preferred. Clays or modified clays work in this respect. Examples of suitable allergen sequestrants include plant lectins with an affinity for N-acetylgalactosamine such as jacalin, peanut, and soybean, where the lectins both bind allergens and are bound to the web, thus removing allergens from a surface. The fluid may also include a fragrance. The fluid may also include a pheromone to either attract or repel an animal. The fluid may also be shoe polish, a carpet cleaning solution, a stain removal fluid, kitchen floor and counter top cleaners, etc.

In other aspects of the present disclosure, one or more first substance blisters 70 may include a first substance, one or more second substance blisters 75 may include a second substance, and so on. In these aspects, the wipe and base layers 15, 20 distribute and/or mix the substances. The device 10 may be adapted to enable one of two cleaning or treating schemes. The first relies on activation chemistry: substances from the first and second substance blisters 70, 75 mix to activate a cleaning or treating composition that has a single cleaning or treating purpose. The first and second substance blisters 70, 75 keep the substances separate until used. The second cleaning or treating scheme enables the ease of application for the completion of task chemistry using substances that are complementary: the first and second substance blisters 70, 75 include substances that are complementary and when used together produce more effective cleaning or treatment results.

In one exemplary aspect of the complementary treatment scheme, a fragrance completes the cleaning job for a consumer by leaving a cue that the task has been completed. Separating the fragrance from an effective, efficient cleaning substance means the cleaning task is completed faster with the same "complete task" cue as that obtained with a longer and more arduous cleaning process. The faster completion results from the cleaning substance not needing to compete with the fragrance and from the cleaning substance not becoming at least partially deactivated by contact with the fragrance while in storage or shipping. In any of these aspects, the cleaning substance may be one or more of a bleach, an oxidation agent, a reduction agent, an anti-microbial agent, or any other suitable cleaning substance.

In the first cleaning or treating scheme, a variety of different reactive chemistries may be utilized. Such reactive chemistries employ a substance in the first substance blister(s) 70 that will react with a substance in the second substance blister(s) 75 to create a third substance that will be effective for cleaning, treating, or other use. Although the first and second substance blisters 70, 75 are referred to in the singular in these examples, there may also be a plurality of first substance blisters 70 and/or a plurality of second substance blisters 75 with affecting the disclosure. Examples of reactive chemistries include, without limitation, the following:

(1) Heat generation for comfort or cleaning. The use of two substances that react exothermically provides heat when the first substance is combined with a second substance. In particular, a weak acid powder, such as citric or malic acid, may be provided by the first substance blister 70 and a weak base, such as sodium bicarbonate, sodium borate, potassium phosphate or sodium citrate, may be provided by the second substance blister 75 to form a solution. The acid and base are balanced to raise the solution temperature for maximum cleaning.

(2) Activation of a peroxide bleach for effective bleaching at ambient temperatures. For example, a monopersulfate peroxygen bleaching compound and a bicyclic or tricyclic diketone bleach activator will react together in aqueous solution to form a dioxirane bleaching composition. Alternatively, a peroxygen bleach may be activated by pH adjustment by creating a pH shift that enhances the bleaching effect of hydrogen peroxide. Hydrogen peroxide lacks adequate storage stability to be a viable consumer product at low pH when sold in an aqueous solution. A weak acid, such as citric acid, may be employed in the form of a dry powder in the first substance blister 70 with hydrogen peroxide in the second substance blister 75 to enhance the bleaching power of the hydrogen peroxide at the target surface. In another example, a dry bleaching composition particularly useful for low temperature applications is provided in which generation of hypochlorite by reaction between a peroxygen bleaching agent and a chloride salt is promoted by an aromatic diol or oxidized aromatic diol activator. Preferred activators are in ester form and provide hypochlorite generation at levels of less than about 20 ppm for at least about the first two minutes following dissolution of the compositions in an aqueous solution, but rising to effective bleaching levels within a reasonable time thereafter. The initially low hypochlorite level assists in the functioning of laundry additives, such as fabric brighteners.

(3) Generation of other bleaches for effective bleaching at ambient temperatures. For example, a chloroisocyanurate disposed in dry form in the first substance blister 70, when combined with a buffer in the second substance blister 75, generates sodium hypochlorite in situ when water is added to the device 10. In this example, the first substance blister 70 with the chloroisocyanurate typically is sealed prior to use to keep humidity out. In another example, sodium hypochlorite can be combined with a buffer, generally at a pH of between about 6.0 and 7.0. The buffer pH may be lower so long as chlorine gas is not generated by the combination. This combination generates hypochlorous acid in situ. Forming hypochlorous acid in situ is advantageous because it has a very short shelf life, and because it is an effective hard surface cleaning substance and disinfectant.

(4) Generation of small amounts of chlorine dioxide or chlorine for in situ bleaching. For example, sodium chloride may be oxidized in an aqueous solution to form chlorine dioxide. In one exemplary aspect of the present disclosure, the first substance blister 70 includes a solution of sodium chlorite while the second substance blister 75 includes an oxidizing substance either as a solid or as a solution. Whether or not a particular reaction of an oxidizing agent and a metal will occur spontaneously may be predicted by reference to a standard table of half reaction potentials such as that in CRC Handbook of Chemistry and Physics (CRC Press). If the sum of the potentials of the oxidation half-reaction and the reduction half-reaction is positive, then the reaction will occur spontaneously.

Limited conversion of sodium chlorite to chlorine dioxide is desirable for most applications in which the device 10 is intended for hard surface sanitation to avoid release of significant amounts of chlorine dioxide gas into the air. The level of chlorine dioxide generated in the cleaning solution delivered by the device 10 at any given time is preferably from about 5 ppm to about 120 ppm, such as from about 10 ppm to about 100 ppm, and such as from about 10 ppm to about 60 ppm. In additional, a limited conversion of chlorite to chlorine dioxide extends the length of time for which the device 10 may produce and sustain levels of chlorine dioxide within the aforementioned range. In general it is preferable that the device 10 sustain a level of chlorine dioxide of between 10 ppm and 120 ppm for a period of from about 30 seconds to about 15 minutes or more. The device 10 may sustain a level of chlorine dioxide such as from about 45 seconds to about 12 minutes, or such as from about 1 minute to about 10 minutes.

(5) General cleaning and air freshening. The first substance blister 70 may include an all-purpose cleaning substance that may be acidic, basic, or including an oxidant, and may include water and/or a surfactant. The second substance blister 75 may include a microencapsulated fragrance ingredient for air freshening. In use, the ionic strength of the cleaning solution causes the fragrance ingredient to migrate to the air/liquid interface and bloom. This would provide an efficient and effective delivery of fragrance without excessive loss of intensity due to dilution in the cleaning solution. The encapsulated storage of the fragrance ingredient avoids any issue of fragrance incompatibility with the cleaning solution.

(6) Visual indication of disinfection. The first substance blister 70 may include a peroxide or hypochlorite bleach and the second substance blister 75 may include a weak dye that decolorizes in a short time when exposed to the bleach. The disappearing dye color gives the user a timer for disinfectant action. Disinfectants need a span of time while wet on the surface to actually achieve desirable bacteria kill levels. Instructions and timing with respect to disinfectants are government-regulated. A user-friendly timing system resident in the device 10 helps to ensure that government regulations are met by the user without the user needing to know about the requirements or even the existence of such regulations.

(7) Epoxy finishes. Many light-, moisture-, and oxygen-initiated epoxy reactions provide stain repellency or other protective finishes. In simplistic terms, an epoxy is typically formed by combining two epoxy reactants and then applying the mixture to a surface. One epoxy reactant may be provided by the first substance blister 70 and the other epoxy reactant may be provided by the second substance blister 75. Ambient conditions would provide the initiator for the reaction.

In another aspect of the present disclosure, the epoxy device includes a catalyst system. Both epoxy reactants are provided in the first substance blister 70 and the catalyst element is provided in the second substance blister 75. As the concentration of the catalyst is not important to the epoxy reaction product other than to affect the rate, variation in the amount of catalyst applied may have less of an impact on final quality than if the two epoxy reactants are supplied separately.

In one exemplary aspect, the first substance blister 70 may include a 1:1 molar blend of a glycidyl ester functional resin such as GMA 207-SA available from Reichhold Chemical and a carboxyl functional acrylic resin such as Joncryl 819 available from Johnson Polymer. The resins may be applied to the device 10 without additional substances or may be incorporated with an appropriate volatile organic solvent. The second substance blister 75 may include a catalyst such as 2-ethylhexyl amine, 2-ethylimidazole, or a similar compound. When the blisters 70, 75 are burst, the glycidyl ester functional resin and the carboxyl functional acrylic resin are mixed with the amine catalyst to catalyze the reaction between the glycidyl ester functional resin and the carboxyl functional acrylic resin.

Within the scope of the present disclosure is further treating the target surface with heat to assist the crosslinking reaction of the epoxy. For example, a small metal part may be wiped with the device 10 and then placed in a curing oven at a temperature of from about 100° C. to about 200° C. or more to facilitate the crosslinking reaction. In general, the epoxy reactants include a diglycidyl ether or other chemical compounds including oligomeric species including two or more unreacted epoxy groups. Bisphenol A glycidylether and its oligomers are especially preferred. Another class of commonly used materials is glycidyl ester resins, especially preferred are the glycidyl ester functional acrylic resins. These substances may be homopolymerized or reacted with active hydrogen including compounds such as carboxyl or anhydride groups. Both homogeneous and heterogeneous crosslinking may occur without a catalyst but may be minimized by appropriate control of storage conditions such as pH. Catalysts are used to facilitate the crosslinking reaction. Such catalysts include amine and phosphonium functional compounds such as 2-ethylhexyl amine, Bis-(2-ethylhexyl) amine, tetrabutylphosphonium bromide, 2-ethylimidazole, tetramethyl guanidine, and benzyltrimethylammonium bromide. In addition, various metal salts known in the art may also be used. Especially preferred are zinc and zirconium salts such as zinc acetate, zinc acetyacetonate, and zirconium octonoate.

(8) Foaming reaction for suds generation. Any substance combination releasing carbon dioxide or harmless gas during the reaction may be used. For example, sodium bicarbonate, calcium carbonate or sodium bicarbonate embedded with citric acid powder may be used to boost foaming in a surfactant system. The foam may be made to dissipate quickly, but would still provide an active cleaning signal to the user. The first substance blister 70 includes an acid or base substance in conjunction with a foaming surfactant. The second substance blister 75 includes a substance having a pH more acidic or more basic than the substance in the first substance blister 70. Whether a basic or acidic system is used in the first substance blister 70 depends upon the natures of the surfactant, of the acidic or basic species, and of the surface being cleaned. In one exemplary aspect of the present disclosure, a basic species is selected from the group of carbonate or bicarbonate salts. Such salts react with acid to generate carbon dioxide and assist in foam development. When a surface is first wiped by an acidic or basic substance combined with a substance having an opposite pH classification, the neutralization reaction that occurs forms carbon dioxide and assists in the development of foam.

In an example of surface-specific use, the first substance blister 70 may include an acidic system for use on surfaces best cleaned under acidic conditions, such as brass, copper, and other metals, or for use in removing an appropriate substance from a surface, such as removing metal, rust, or hard water staining from glass. The second substance from the second substance blister 75 is then wiped on the surface to complete the cleaning and neutralize the acid.

In another example of a surface-specific use, the first substance blister 70 includes a basic system for use on surfaces best cleaned under basic conditions, such as ceramics, glass, and some plastics and coatings. A basic system is particularly useful for removing grease and greasy residues. The second substance from the second substance blister 75 is then wiped on the surface to complete the cleaning and neutralize the base. These examples make a universal and multi-functional device 10.

In another example, isocyanurate or any other source of sodium hypochlorite is disposed in dry form in the first substance blister 70, and a peroxide/surfactant blend is disposed in the second substance blister 75. The combination of these substances generates oxygen, causing the surfactant to foam.

A foaming surfactant may be defined as one preferably having a foam height greater than 10 mm when measured according to the Ross-Miles method in the case of a solution including 0.02% by weight of surfactant (active substance) in distilled water at 25° C. Examples of such surfactants include foaming anionic surfactants. Exemplary foaming anionic surfactants include alkyl phosphates such as sodium lauryl phosphate; alkyl taurates such as sodium methyl palmitoyl taurate; sulfosuccinates such as cocoyl sulfosuccinate; alkyl sulphates such as triethanolamine lauryl sulfate; alkyl ether sulfates such as sodium lauryl sulphate; and alkyl ether carboxylates such as alkyloxy sodium decyl ether carboxylate. The foaming surfactant may also be non-ionic. Exemplary nonionic foaming surfactants include polyglyceryl alkyl ethers such as polyglycerolated dodecanediol and alkylglucosides such as dodecyl glucoside. The surfactant may also be cationic. Examples of cationic foaming surfactants include to amine oxides and quaternary ammonium salts such as polyquaternium 22. Exemplary amphoteric foaming surfactants include disodium cocoamphodiacetate, cocamidopropylbetaine, and cocobetaine.

(9) Precipitation reaction. Enhanced cleaning may be achieved by in-situ generation of an abrasive substance. In this aspect of the present disclosure, the user may decide whether or not the cleaning device is used as an abrasive cleaning article or a non-abrasive cleaning article. For example, the first substance blister 70 may include an aqueous solution of a soluble salt. The second substance blister 75 includes a solution of a second soluble salt selected such that the combination of the first soluble salt solution with the second soluble salt solution creates an insoluble precipitate. In one exemplary aspect, the first substance blister 70 of the device 10 includes a solution of a soluble calcium salt such as calcium chloride. The second substance blister 75 of the device 10 includes a solution of a soluble carbonate salt such as sodium carbonate. When the first and second substance blisters 70, 75 are burst, the calcium chloride solution is mixed with the sodium carbonate solution to form an insoluble precipitate of calcium carbonate. This insoluble precipitate serves as an abrasive agent. Either the first or second substance blister 70, 75 may be used independently as a non-abrasive cleaning implement. It is only when both the first and second substance blisters 70, 75 are used that an abrasive cleaning implement is achieved.

In another aspect of the present disclosure, one of the substances may be present in solid form in the device 10. The specific salts are selected such that an insoluble precipitate may be formed. The salts may be employed in conjunction with surfactants and/or any other cleaning formulations. The salts and surfactant are selected such that interaction between either of the salts and the surfactant does not deactivate the surfactant. In one exemplary aspect, calcium chloride is used as one of the salts, and the surfactant is preferably selected from a non-ionic or cationic surfactant to avoid precipitation of the calcium salt with the surfactant. As another example, the combination of sodium lauryl sulfate and soluble calcium salts will react to form calcium lauryl sulfate such that the surfactant properties of the original sodium lauryl sulfate will be lost.

In use, a user squeezes one or more blisters 50 within the device 10, causing the blister(s) to burst and release the substance(s) stored therein. The user can then use the device 10 to clean, polish, etc., depending on its intended use. In some cases, the user may select how much of a substance to release by following instructions or marking included on or with the device 10. In other cases, the user can decide whether to release one or more substances by following instructions or markings included on or with the device 10.

In various aspects, the device 10 may include or be accompanied by informational items such as instructions in the use of the device 10 and tips for cleaning, skin care, etc. depending on the intended use of the device 10. As used herein, the term "informational item" refers to objects that are provided on or in addition to the device 10, and that are adapted to communicate information to the user and/or consumer of the device 10. Examples of informational items include cards, paper, electronic media, printing on the packaging, or other suitable media capable of storing and conveying information. The informational item may be printed on or attached to the device 10, or may accompany the device 10 by being on or within the packaging for the device 10.

In various aspects, the informational items associated with the device 10 may be adapted to appeal to the specific category of user and/or purchaser to which the device 10 is adapted. The informational items may be adapted, for example, by providing information likely to be of interest to a given category of user and/or purchaser.

For example, a device 10 may be adapted for use by a caregiver for bathing a baby. An informational item may be associated with the device 10 that is adapted to interest caregivers. For example, the informational item may be a card containing information or instructions about children's health and hygiene, such as sleep habits, thumb sucking, teething, skin health, toilet training; questions to ask a child; jokes; and the like, and combinations thereof. The informational item may additionally or alternatively include addresses for web sites available on the Internet. The web sites may contain information related to issues of interest for caregivers and users of devices 10.

The informational item may additionally or alternatively include information describing activities that are suitable for caregivers and users of devices 10. The activities may be adapted for a subject at a specific age, size and/or stage of development. For example, the activities may be adapted to promote interaction between the child and the caregiver.

The informational item may additionally or alternatively include information describing the benefits to be derived from using the device 10. This informational item would be part of a promotional plan emphasizing the customizability of the device 10 for the benefit of the consumer, caregiver, and/or user. This informational item would both explain the use of the various components of the device 10 as well as present the additional components that may be available and the various combinations that are possible to achieve different goals.

Aspects of the disclosure have been described with reference to various specific and illustrative aspects and techniques. However, it should be understood that many variations and modifications may be made while remaining within the spirit and scope. Accordingly, this is intended to embrace all such alternatives, modifications and variations that fall within the spirit and scope of the appended claims.

We claim:

1. A device comprising:
   a base layer;
   a wipe layer attached to the base layer to define an interior space between the wipe and base layers;
   a plurality of blisters positioned within the interior space, each blister having a blister volume, wherein the sum of the blister volumes is a total blister volume; and
   an indication disposed on the wipe layer or the base layer corresponding to a single blister or a group of blisters indicating the ratio of the blister volume of that single blister or the sum of the blister volumes of that group of blisters to the total blister volume.

2. The device of claim 1, wherein the ratio is indicated by printing on the wipe layer or the base layer.

3. The device of claim 1, wherein the ratio is indicated by the shape of the blisters.

4. The device of claim 1, further comprising a barrier layer interposed between the wipe layer and the base layer.

5. The device of claim 1, wherein the device is a wipe.

6. The device of claim 1, wherein the device is a mitt.

7. The device of claim 1, wherein the wipe layer and the base layer are two portions of the same piece of material.

\* \* \* \* \*